United States Patent [19]

Chouinard et al.

[11] Patent Number: 5,885,615
[45] Date of Patent: Mar. 23, 1999

[54] PHARMACEUTICAL CONTROLLED RELEASE TABLETS CONTAINING A CARRIER MADE OF CROSS-LINKED AMYLOSE AND HYDROXYPROPYLMETHYLCELLULOSE

[75] Inventors: Francois Chouinard, Laval; Wilfrid Jacques, Longueuil, both of Canada

[73] Assignee: Labopharm Inc., Sainte-Therese, Canada

[21] Appl. No.: 699,611

[22] Filed: Aug. 19, 1996

[30] Foreign Application Priority Data

Apr. 10, 1996 [CA] Canada ................................ 2173818

[51] Int. Cl.⁶ .......................... A61K 9/22; A61K 47/36; A61K 47/38
[52] U.S. Cl. ...................... 424/465; 424/468; 514/960
[58] Field of Search ................ 424/484, 486, 424/488, 464, 465, 468, 469; 514/960, 964, 965

[56] References Cited

U.S. PATENT DOCUMENTS

| | | |
|---|---|---|
| 3,065,143 | 11/1962 | Christenson et al. . |
| 4,167,558 | 9/1979 | Sheth et al. . |
| 4,389,393 | 6/1983 | Schor et al. . |
| 4,610,870 | 9/1986 | Jain et al. . |
| 4,704,285 | 11/1987 | Alderman . |
| 4,734,285 | 3/1988 | Alderman et al. . |
| 4,775,535 | 10/1988 | Lowey . |
| 4,855,143 | 8/1989 | Lowey . |
| 5,456,921 | 10/1995 | Mateescu et al. . |
| 5,603,956 | 2/1997 | Mateescu et al. .................... 424/488 |
| 5,616,343 | 4/1997 | Cartilier et al. ..................... 424/464 |
| 5,629,018 | 5/1997 | Besemer et al. ..................... 424/488 |
| 5,780,057 | 7/1998 | Conte et al. ........................ 464/468 |

Primary Examiner—Robert H. Harrison
Attorney, Agent, or Firm—Foley & Lardner

[57] ABSTRACT

Disclosed is a pharmaceutical controlled release tablet containing an active ingredient in combination with a carrier made of cross-linked amylose in which hydroxymethylpropylcellulose (HPMC) with a viscosity higher than or equal to 4000 cps is added as an adjuvant. The addition of HPMC to the tablet permits to control the effect of enzymes, and more particular alpha-amylase present in the intestinal medium, on the cross-linked amylose used as a carrier, and thus to reduce the dependence of the kinetics of release upon the concentration of enzymes present in the medium.

22 Claims, 4 Drawing Sheets

PHARMACEUTICAL CONTROLLED RELEASE TABLETS CONTAINING A CARRIER MADE OF CROSS-LINKED AMYLOSE AND HYDROXYPROPYLMETHYLCELLULOSE

FIELD OF THE INVENTION

The present invention is related to the subject matter of described and claimed in Canadian patent No. 2,041,774 issued on Apr. 19, 1994 and U.S. Pat. No. 5,456,921 issued on Oct. 10, 1995, both of which are incorporated by reference herein in their entirety.

More precisely, the invention relates to a pharmaceutical controlled release tablet containing an active ingredient in combination with a carrier made of cross-linked amylose in which hydroxymethylpropylcellulose (HPMC) with a viscosity higher than or equal to 4000 cps is added as an adjuvant.

The invention also relates to the use of HPMC with a viscosity equal to or higher than 4000 cps as an adjuvant in a tablet of the type described hereinabove for the purpose of controlling the effect of enzymes, and more particularly alpha-amylase present in the intestinal medium, on cross-linked amylose and thereby reducing the dependence of the kinetics of release upon the concentration of enzymes present in the medium.

BRIEF DESCRIPTION OF RELATED ART

Canadian patent No. 2,041,774 and U.S. Pat. No. 5,456,921 mentioned hereinabove both describe pharmaceutical compressed tablets for oral administration of a dose of one or more active ingredients for the purpose of delivering or releasing said dose at a controlled rate over a given time period. Such tablets are described as containing, for example, up to 60% by weight of one or more active ingredients which may be of any nature. Such tablets also contain, for example, at least 40% by weight of a vehicle or carrier consisting of amylose cross-linked with a suitable cross-linking agent. The cross-linking agent can be present, for example, in quantities corresponding to 0.1 to 10 grams of cross-linking agent per 100 grams of amylose, the preferred quantity of cross-linking agent being 0.5 to 7.5 grams and even more preferably being 1 to 6 grams per 100 grams of amylose. Such cross-linked amylose, which is known under the name Contramid®, is preferably, eventhough not necessarily, obtained using epichlorohydrin or 2,3-dibromopropanol as cross-linking agents, since amylose cross-linked with these two agents has been approved for several years by most food and drug control organisations including the U.S. Food and Drug Administration.

The main advantage of cross-linked amylose such as Contramid® lies in that it maintains a constant release rate (zero order kinetics), contrary to most carriers currently used in compressed tablets for controlled release, where the active ingredient is released by diffusion, following a Fickian release kinetics (the cumulative released fraction is proportional to the square root of time).

From a practical standpoint, in an aqueous medium, cross-linked amylose such as Contramid® forms a porous hydrogel that acts as a carrier for the active ingredient and provides a controlled release of the latter following oral administration. In an intestinal medium, this hydrogel is sensitive to the action of digestive enzymes which attack the amylose chains and degrade the tablet, ensuring its disintegration in the digestive tract. The alpha-amylase enzyme is, in this regard, particularly effective in accelerating the release of active ingredients from the tablets, and its use as an adjuvant in the preparation of tablets forms the subject matter of an international patent application published on Feb. 3, 1994 under No. WO 94/02121, the disclosure of which is incorporated by reference herein in its entirety.

Tablets produced in this way are efficient and provide an adequate controlled release in most of the patients. Yet there is a certain disparity from one patient to the other, owing to the fact that enzymatic activity varies considerably among individuals and as a function of food intake. Because cross-linked amylose such as Contramid® is sensitive to pancreatic amylase, this variability is a potential drawback to the marketing of such tablets, at least with some active ingredients.

The addition of an adjuvant allowing for a control of the effect of enzymes would therefore represent an important asset for one who wishes to make full use of the unique properties of cross-linked amylose such as Contramid® on an industrial scale.

SUMMARY OF THE INVENTION

The present invention is based on a very surprising discovery made by the inventors that the addition of a very specific adjuvant to Contramid® in a certain amount, permits protection of the resulting pharmaceutical tablets against any major variation in the rate of release of the drug due to the degradation of cross-linked amylose such as Contramid® by the enzymes present in the intestinal medium.

This very specific adjuvant is a well known hydrogel that is currently used in the pharmaceutical field, viz. hydroxypropylmethylcellulose (HPMC). However, this adjuvant is efficient only when its viscosity is equal to or higher than about 4000 centipoises (cps) and when the amount of it that is added to the tablet is ranging between about 10 and about 30% by weight with respect to the total weight of the tablet. Below about 10%, the amount of HPMC added to the tablet may prove unsatisfactory. Above about 30%, the amount of HPMC may be too high and may affect the carrier, which is no more mainly made on cross-linked amylose such as Contramid® thereby leading to a release of Fickian kinetics.

In accordance with the invention, it has been discovered that the addition of HPMC with a viscosity equal to or higher than about 4000 cps to cross-linked amylose such as Contramid® imparts the same properties that are unique and unexpected and could not have been inferred from what is presently known on this product, viz. a higher resistance to the enzymatic medium and a lower dependence of the kinetics of release upon the concentration of enzymes present in the medium.

This discovery is surprising inasmuch as similar tests carried out by adding other kinds of polymers used in the pharmaceutical field and considered as possible substitutes for HPMC, such as ethylcellulose, methylcellulose, hydroxypropylcellulose (HPC) or Carbomer, have given negative results as will be shown hereinafter.

Therefore, a first object of the present invention is to provide the pharmaceutical controlled release tablet for the oral administration of a given amount of at least one active ingredient. The tablet comprises up to about 60% (e.g., 60%) by weight of the active ingredient mixed and compressed with at least about 40% (e.g., 40%) by weight of a carrier containing amylose cross-linked an amount of cross-linking agent sufficient to provide prolonged release of the active ingredient (when compared to release rate of the tableted active ingredient itself), for example, from about 0.1 to about 10 (e.g., 0.1 to 10) grams of a cross-linking agent per 100 grams of amylose. In accordance with the invention, the carrier actually contains:

from about 30 to about 90% (e.g., from 30 to 90%) of cross-linked amylose; and from about 10 to about 30% (e.g., from 10 to 30%) of hydroxypropylmethylcellulose (HPMC) with a viscosity equal to or higher than about 4000 cps, the above percentages being expressed by weight with respect to the total weight of the tablet.

A second object of the invention is to provide a method for controlling the effect of enzymes onto a carrier of a pharmaceutical controlled release tablet for oral administration to a patient, the tablet containing up to 60% by weight of at least one active ingredient and at least 40% by weight of a carrier containing amylose cross-linked with 0.1 to 10 grams of a cross-linking agent per 100 grams of amylose. This method comprises the step of adding hydroxypropylmethylcellulose (HPMC) with a viscosity equal to or higher than about 4000 cps as an adjuvant to the carrier, whereby the viscosity is measured in a 2% water solution at a temperature of 20° C.±0.1° C.

The tablets that are so-obtained have an excellent resistance to the enzymic medium and a much lower dependence to the concentration of enzymes in the medium. They also have a better mechanical resistance in use, which is an advantage from a commercial standpoint.

The invention and its numerous advantages will be better understood upon reading the following non-restrictive description, which includes the results of some tests made by the inventors.

GENERAL DESCRIPTION OF THE INVENTION

Figure 1:
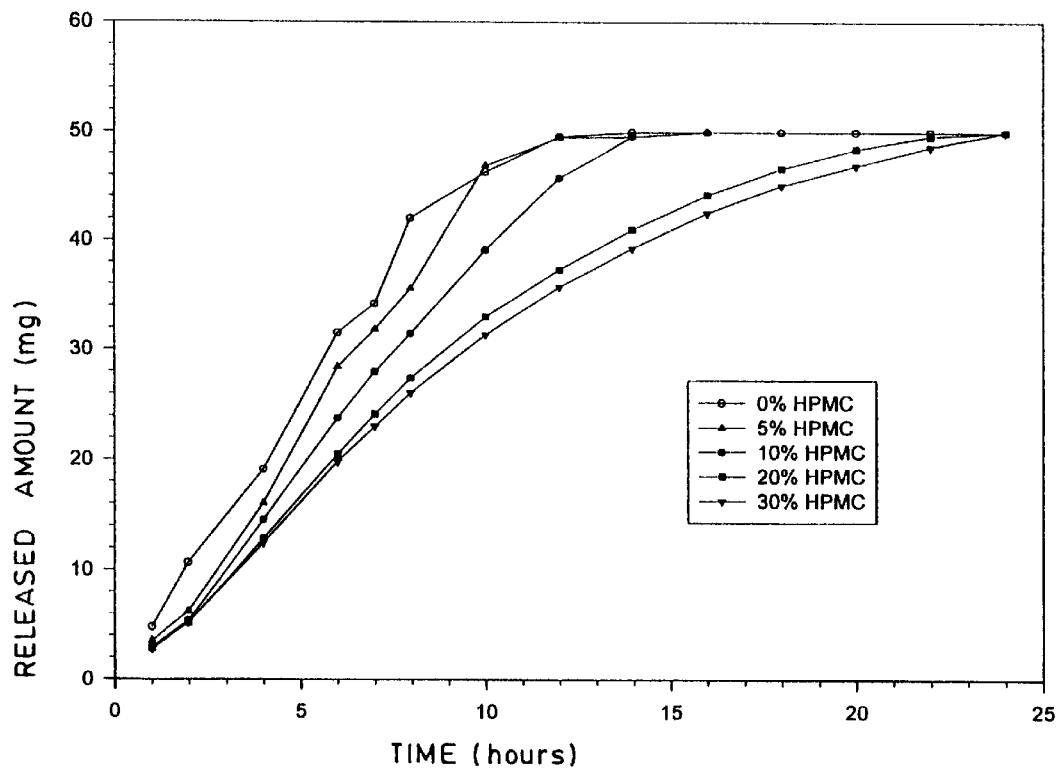
FIG. 1 is a curve illustrating the dissolution profile of 500 g compressed tablets containing 50 mg ASA, Contramid® and different concentrations of HPMC 2208/100000, where the phosphate buffer contained 18 I.U./ml of enzyme.

As described previously, the invention is concerned with the preparation of pharmaceutical compressed tablets for oral administration of one or more active ingredients for the purpose of obtaining a controlled release of the active ingredients over a given period of time. Such compressed tablets contain, for example, up to 60% by weight of one or more active ingredients mixed and compressed with at least 40% by weight of a carrier made of amylose cross-linked with a suitable cross-linking agent in a quantity corresponding to 0.1 to 10 grams of cross-linking agent per 100 grams of amylose.

By "controlled release", there is meant a release at a quasi-constant (linear) rate for a period, which can extend up to 20 hours and beyond.

The active ingredients used in the tablet can be of any type that can be administered orally. A non-restrictive list of examples includes sedatives, antacids, antiinflammatory agents, vasodilators, stimulants, antihistamines, decongestants, vasoconstrictors, anticoagulants, antiarrythmics, antihypertensives, ansnolic agents, hyper or hypoglycaemic agents, diuretics, antiasthmatic agents, antipyretics, antiemetic, antispasmodics, etc . . . .

The cross-linked amylose such as Contramid® is present in the form of particles. Preferably, at least about 50% (e.g., 50%) of these particles have a size comprised between about 25 and about 700 microns (e.g., between 25 and 700 microns).

The active ingredient, which is preferably in the form of a powder, is mixed with a carrier made of Contramid® and the mixture obtained in this way is then compressed to obtain the desired tablets. The compression is preferably made at a pressure of about 0.15 tons per $cm^2$ (e.g., 0.15 tons per $cm^2$).

One aspect of the invention is that the carrier of cross-linked amylose for the preparation of the compressed tablets, actually contains from about 30 to about 90% (e.g., from 30 to 90%)of cross-linked amylose such as Contramid® and from about 10 to about 30% (e.g., from 10 to 30%) of hydroxypropylmethyl-cellulose (HPMC) having a viscosity equal to or higher than about 4000 cps (e.g., 4000 cps), the percentages being expressed by weight with respect to the total weight of the tablet. The HPMC conforms to USP standards, Grade XXIII, and the viscosity is measured in accordance with these standards in a 2% water solution at a temperature of 20° C.≅0.1° C.

The HPMC that is used is preferably chosen among the HPMC's identified by numbers 2208 and 2910 in the U.S. Pharmacopedia, 23rd edition.

HPMC 2208 has a methoxyl content ranging form 19 to 24% and a hydroxypropoxyl content ranging from 4 to 12%. By way of example, this product is marketed with viscosities of 100, 4000, 15000 and 100000 cps by THE DOW CHEMICAL CO. under the trademark Methocel® E-4M, 15M and 100M.

HPMC 2910 has a methoxyl content ranging from 28 to 30% and a hydroxypropoxyl content ranging from 7 to 12%. By way of example, this product is marketed with viscosities of 4000 and 100000 cps by THE DOW CHEMICAL CO. under the trademarks Methocel® E-4M and 100M.

The carrier of cross-linked amylose may also contain one or more other ingredients currently used in the preparation of pharmaceutical compressed tablets, including:

fillers such as lactose or sucrose, in quantities not exceeding about 40% (e.g., 40%) by weight;

glidants such as silicium dioxide, in quantises not exceeding about 10% (e.g., 10%) by weight;

binders, in quantities not exceeding about 10% (e.g., 10%) by weight;

lubricants and anti-adherents such as magnesium stearate, in quantities not exceeding about 5% (e.g., 5%) by weight; and disintegrants, in quantities not exceeding about 5% (e.g., 5%) by weight.

The compressed tablets may be of the matrix or dry coated (double core) type.

In the first case, the HPMC that is used is preferably chosen among the HPMC 2208 and 2910 having a viscosity higher than 4000 cps. Preferably, HPMC 2208 with a viscosity of 100000 cps will be chosen.

In the second case, viz. of dry coated tablets, the HPMC that is used is preferably chosen also amount the HPMC 2208 and 2910, the viscosity of which may not only be higher than but also equal to 4000 cps. These dry coated compressed tablets comprise an inner core containing a given amount of active ingredient and an external coating containing another amount of the same or another active ingredient mixed and compressed with a carrier containing cross-linked amylose and HPMC. The core also may include a carrier containing of cross-linked amylose and HPMC.

The dry coated tablets are particularly useful because their coating gives a higher flexibility in the release kinetics, which may be slow at the beginning and faster at the end or vice-versa, and a higher active ingredient loading, especially when the above ingredient is highly soluble in water. In most cases, such tablets ensure a two-step release kinetics.

As previously indicated, HPMC, like some other polymers such as hydroxypropylcellulose (HPC) or Carbomer (like the one marketed by B.F. GOODRICH under the trademark Carbopol®), are already currently used for the manufacture of tablets when one wants to obtain a controlled release of an active ingredient. In this connection, one can refer, by way of non-restrictive examples, to U.S. Pat. No. 3,065,143 issued on 1962 and Canadian patent No. 1,188, 614 issued in 1985.

U.S. Pat. No. 3,065,143 teaches that HPMC may be used for the preparation of controlled release compressed tablets, provided that it is used in quantities higher than 30% by weight. This patent also teaches that HPMC forms a mucilaginous barrier made of gum swollen under the action of water, the progressive erosion of which in the gastrointestinal tract provides for the desired controlled release (see example 1 giving disintegration times in vitro). This patent mentions a slow disintegration of the compressed tablets with subsequent release of the active ingredient over a period of more than 4 hours. This differs from the present invention where the compressed tablets hardly swell and do not disintegrate over a period of more than 20 hours in vitro in an enzymatic medium. In addition, the release time in the case of the compressed tablets of the invention is substantially longer than in U.S. Pat. No. 3,065,143.

Canadian patent No. 1,188,614 teaches that HPMC may be used with minor excipients to prepare compressed tablets containing 70 to 95% of active ingredient while obtaining a slow release in vitro. This system, like the one mentioned in U.S. Pat. No. 3,065,143, forms a "soft mucilaginous gel barrier" that releases the active ingredient by diffusion according to a Fickian kinetics (the cumulative released fraction is proportional to the square root of time). This patent does not suggest to use HPMC to confer to a tablet made of cross-linked amylose a resistance toward the action of the enzyme alpha-amylase present in the intestinal fluids.

In contrast to the compressed tablets described in Canadian patent No. 1,188,614, the compressed tablets containing cross-linked amylose and HPMC according to the present invention, remain in their original shape when placed in an aqueous medium for the time necessary to release the active ingredient, for example, for at least 24 hours. No mucilage is formed and the release generally has a constant rate (zero order kinetics) and lasts for a longer time period than in the case of the examples of Canadian patent No. 1,188,614. Therefore, it is not the same technology.

In order to demonstrate the accuracy of the preceding assertions and information, experiments were performed by the inventors.

Compressed tablets manufacturing

For the experiments of pharmaceutical compressed tablets of the matrix and dry coated types including Contramid® as a carrier with or without the addition of HPMC were prepared using the technology described in detail in Canadian patent No. 2,041,774. Other gelifying polymers were also tested to allow for comparison.

All the matrix type compressed tablets had a weight of 500 mg and contained 50 mg of acetylsalycilic acid (ASA) as an example of active ingredient. HPMC at a concentration ranging from 0 to 30% by weight and Contramid® at a concentration ranging from 60 to 90% by weight were used together with 0.25% magnesium stearate as an anti-adhesive agent. The compressed tablets were of the biconvex flat cylindrical type, with a diameter of 12.7 mm.

The Contramid® used for manufacturing the compressed tablets was prepared by using 3.5 grams of epichlorohydrin as a cross-linking agent per 100 grams of amylose, according of the procedure described in detail in Canadian patent No. 2,041,774.

The dry coated compressed tablets had a core containing 128 mg of pseudoephedrin hydrochloride as an example of an active ingredient, mixed with 44 mg of Contramid® used as a carrier. The core was surrounded by a coating containing 72 mg pseudoephedrin hydrochloride, 406 mg of Contramid® and 120 mg (20%) of HPMC 2208/100000. The Contramid® used for manufacturing these compressed tablets was prepared by using 3.5 grams of epichlorohydrin as a cross-linking agent per 100 grams of amylose according to the procedure described in detail in Canadian patent No. 2,041,774.

HPMC's being found in different viscosities, their denominations have been abbreviated in the following way:

HPMC 2208 100 cps=HPMC 2208/100

HPMC 2208 4000 cps=HPMC 2208/4000

HPMC 2008 100000 cps=HPMC 2208/100000

HPMC 2910 4000 cps=HPMC 2910/4000

In vitro assay

The dissolution of the active ingredient from the compressed tablets prepared as described hereinabove, was determined under stirring at 37° C. All experiments were conducted at least in duplicate and the dissolution conditions were as follows:

| Apparatus: | USP dissolution apparatus type 3 |
|---|---|
| Stirring: | 10 dips per minute |
| Dissolution medium: | 2 hours in an acidic medium (pH 1.2); 12 hours in a phosphate buffer (pH 7.0) with or without enzyme (alpha-amylase from bacillus at a concentration ranging from 0 to 732 I.U./ml); and 10 hours in a phosphate buffer (pH 7.0). |

Figure 2:
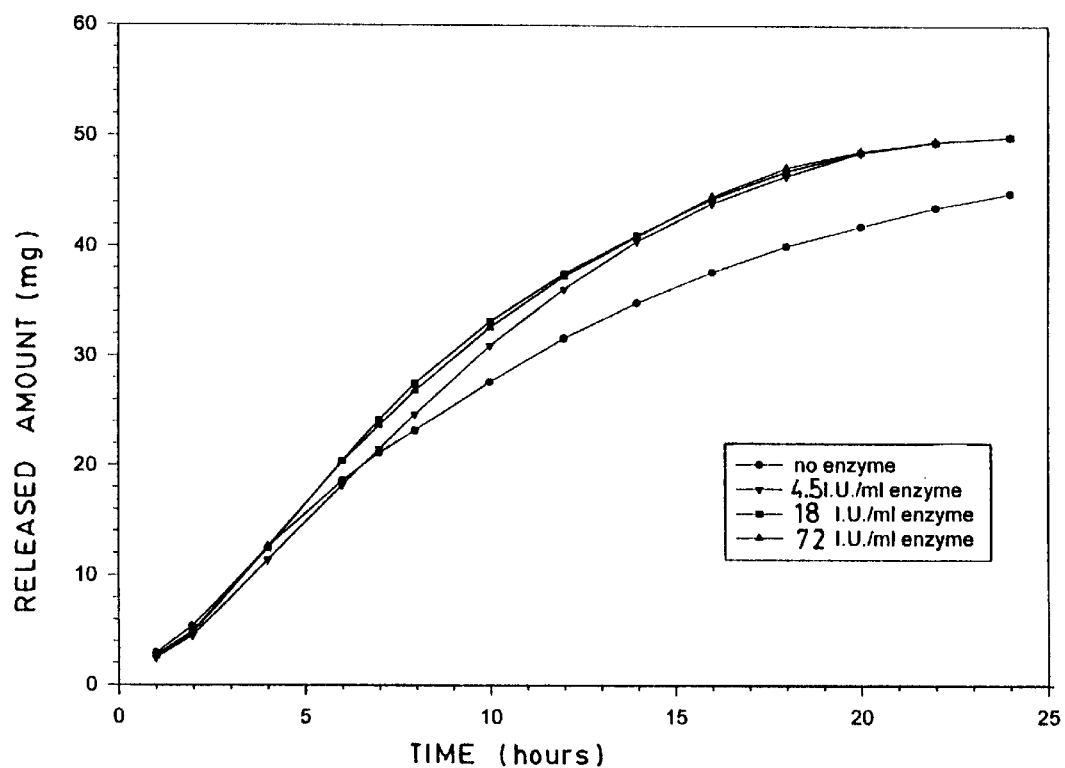
FIG. 2 is a curve illustrating the dissolution profile of 500 mg compressed tablets containing 50 mg ASA, Contramid® and 20% of HPMC 2208/100000, where the phosphate buffer contained different concentrations of enzyme.
Figure 3:
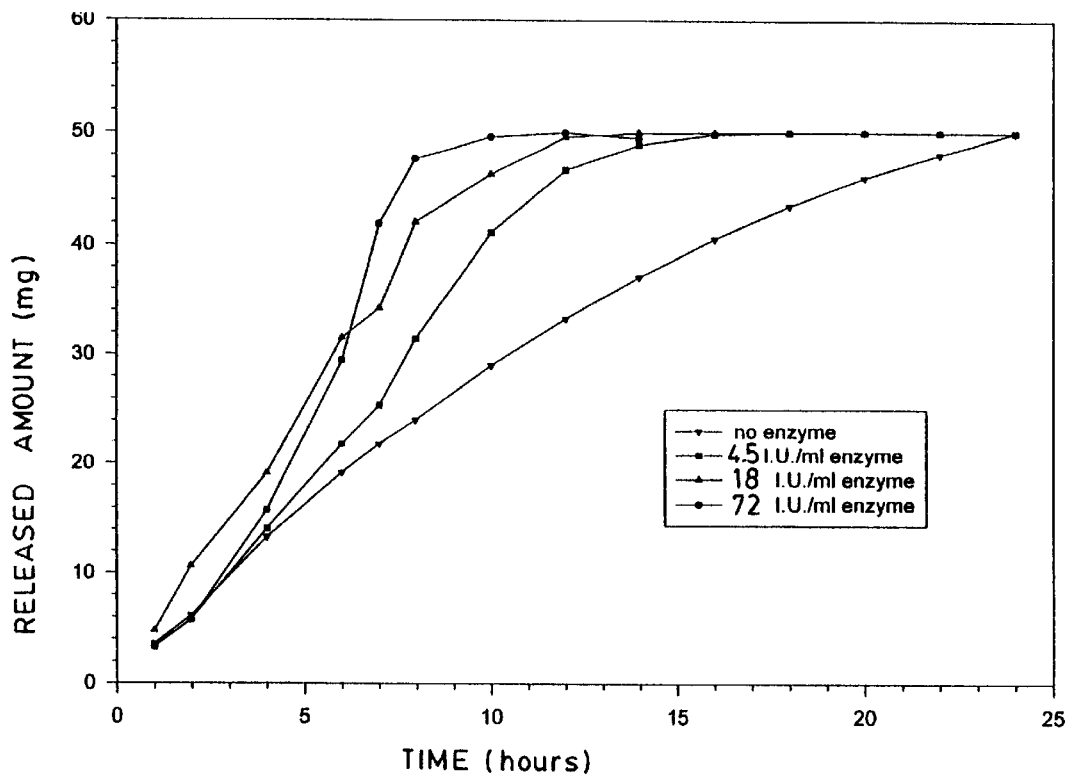
FIG. 3 is a curve illustrating the dissolution profile of 500 mg compressed tablets containing 50 mg ASA, Contramid® and no HPMC, where the phosphate buffer contained different concentrations of enzyme.
Figure 4:
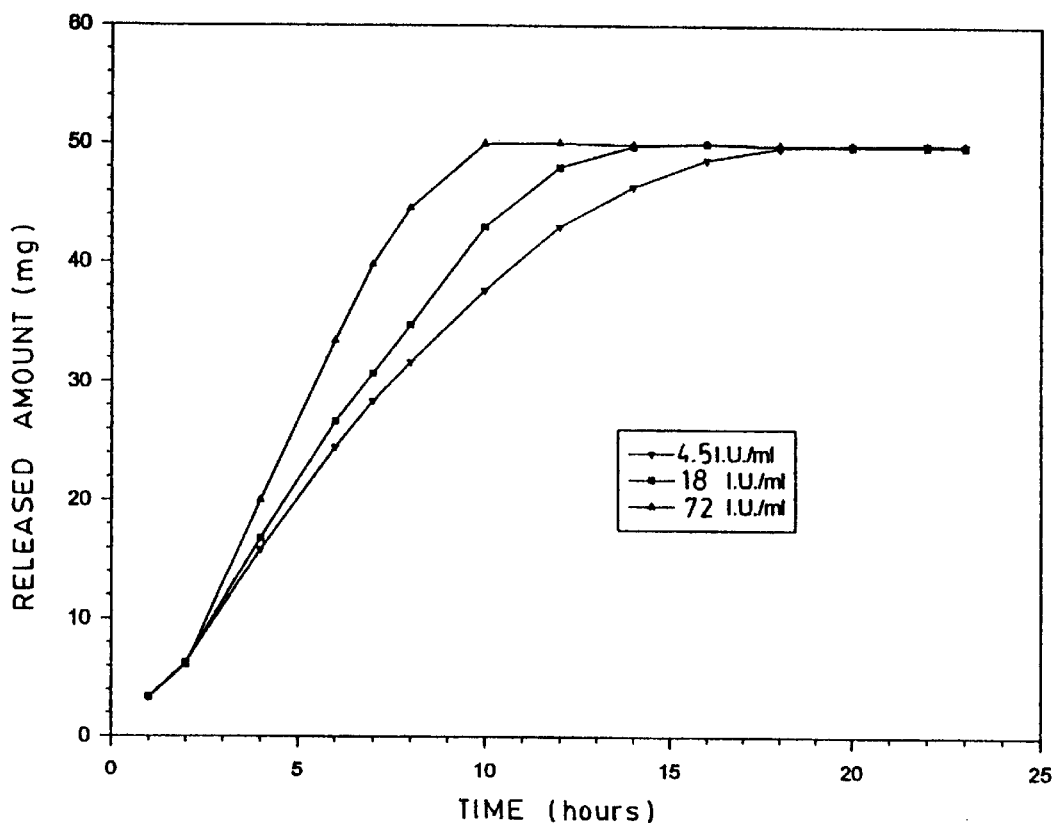
FIG. 4 is a curve illustrating the dissolution profile of 500 mg compressed tablets containing 50 mg ASA, Contramid® and 20% of HPMC 2208/100, where the phosphate buffer contained different concentrations of enzyme.
Figure 5:
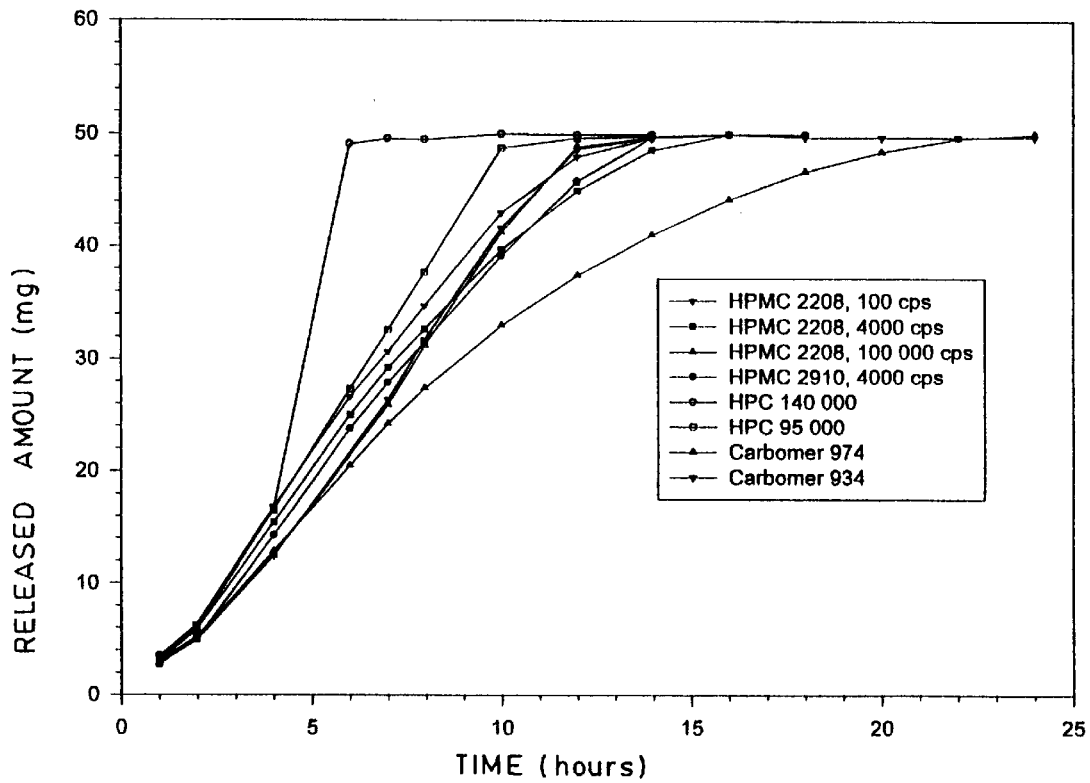
FIG. 5 is a curve illustrating the dissolution profile of 500 mg compressed tablets containing 50 mg ASA, Contramid® and 20% of gelifying polymers, where the phosphate buffer contained 18 I.U./ml of enzyme.
Figure 6:
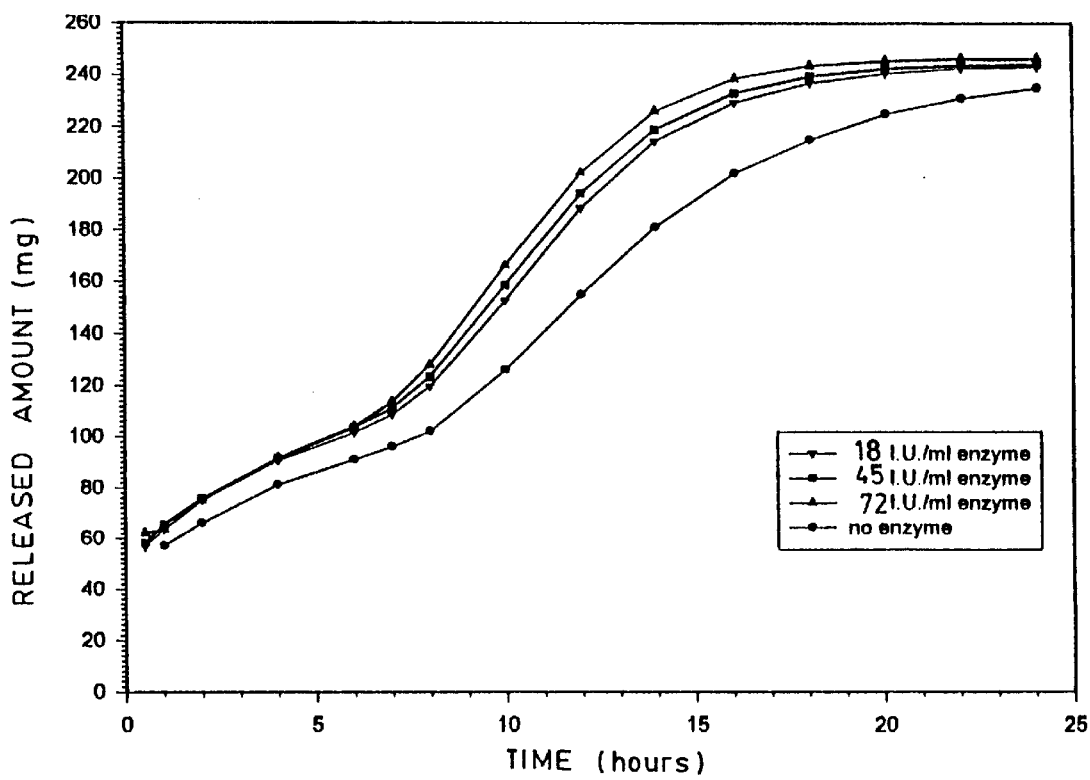
FIG. 6 is a curve illustrating the dissolution profile of dry coated compressed tablets containing pseudoephedrin hydrochloride Contramid® and 20% of different types of HPMC, where the phosphate buffer contained 18 I.U./ml of enzyme.

The results obtained using these experiments are illustrated in the appended drawings in which:

FIG. 1 is a curve illustrating the dissolution profile of 500 g compressed tablets containing 50 mg ASA, Contramid® and different concentrations of HPMC 2208/100000, where the phosphate buffer contained 18 I.U./ml of enzyme;

FIG. 2 is a curve illustrating the dissolution profile of 500 mg compressed tablets containing 50 mg ASA, Contramid® and 20% of HPMC 2208/100000, where the phosphate buffer contained different concentrations of enzyme;

FIG. 3 is a curve illustrating the dissolution profile of 500 mg compressed tablets containing 50 mg ASA, Contramid® and no HPMC, where the phosphate buffer contained different concentrations of enzyme;

FIG. 4 is a curve illustrating the dissolution profile of 500 mg compressed tablets containing 50 mg ASA, Contramid® and 20% of HPMC 2208/100, where the phosphate buffer contained different concentrations of enzyme;

FIG. 5 is a curve illustrating the dissolution profile of 500 mg compressed tablets containing 50 mg ASA, Contramid® and 20% of gelifying polymers, where the phosphate buffer contained 18 I.U./ml of enzyme;

FIG. 6 is a curve illustrating the dissolution profile of dry coated compressed tablets containing pseudoephedrin hydrochloride Contramid® and 20% of different types of HPMC, where the phosphate buffer contained 18 I.U./ml of enzyme.

Matrix type compressed tablets (a) Effect of the concentration of HPMC

In an enzymatic medium at 18 I.U./ml, the concentration of HPMC had a direct effect on the resistance of the compressed tablets to the enzyme and on the release profile of the active ingredient. Whereas at a low concentration (<10%), the compressed tablets had an erratic and poorly reproducible release, above 10% the curve was mere linear. The release time was considerably longer at 20 to 30%.

This demonstrates that the properties of the matrix are dramatically changed when the concentration of HPMC increases. With a minimum of 10% HPMC, the compressed tablets have a better enzymatic resistance giving more linear and more reducible release profiles. At 20% or more of HPMC, the compressed tablets have a very good enzymatic resistance.

(b) Protection against the enzymatic medium

FIGS. 2 and 3 show that HPMC 2208/10000 has a direct effect on the enzymatic resistance of the compressed tablets. When 20% HPMC 2208/100000 was added to the Contramid® carrier, the influence of the enzyme concentration on the profile was very limited eventhough a lower release rate was noted in the total absence of enzyme. The compressed tablets containing no HPMC 2208/100000 were much more sensitive to the enzyme even at a low concentration, whereas in a non-enzymatic medium, the release was nearly identical to the one of a compressed tablet with 20% HPMC 2208/100000. This observation demonstrates that HPMC has no direct effect on the controlled release properties of Contramid® as such, but rather on the sensitivity of the compressed tablets to the enzyme.

By way of comparison, HPMC 2208/100 was tested in similar conditions. FIG. 4 shows that the effect of the enzyme was more pronounced when HPMC had a viscosity of 100 as compared to HPMC with a viscosity of 100000. The molecular weight of HPMC hence is assumed to be a key factor for the resistance to enzymatic degradation.

c) Effect of the type of polymer

Experiments performed with several polymers capable of forming hydrogels in an aqueous medium have revealed the distinctive character of HPMC 2208/100000. FIG. 5 shows that the other tested polymers, including HPMC's with a viscosity equal to 4000 cps, all led to a fast release of the active ingredient. It is hence noted that the optimal protective effect is obtained with high viscosity HPMC.

Dry coated compressed tablets

The results analyzed hereunder are those obtained with dry coated compressed tablets.

FIG. 6 shows that dry coated tablets have good resistance to the enzymatic medium when containing HPMC 2208/100000.

Figure 7:
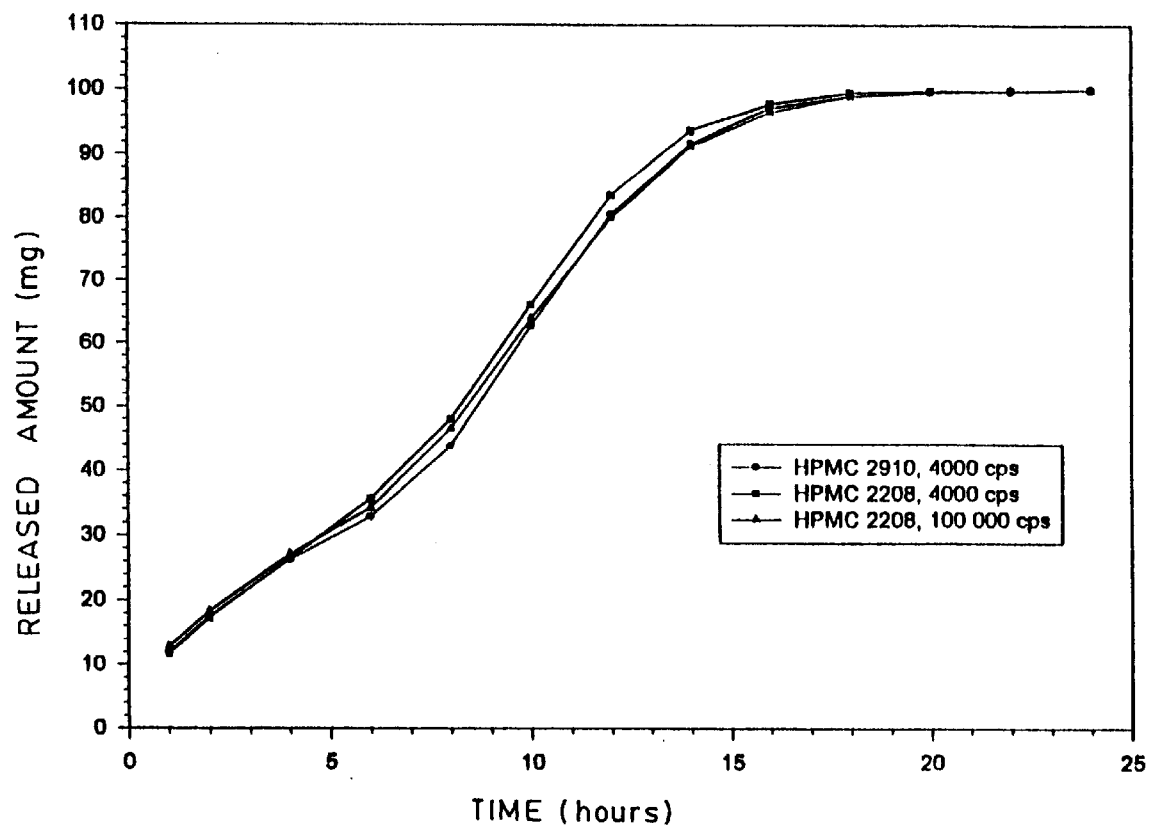
FIG. 7 further shows that the resistance effect illustrated in FIG. 6 is equally pronounced when HPMC with a viscosity as low as 4000 cps is used.

FIG. 7 further shows that this protective effect is equally pronounced when HPMC with a viscosity as low as 4000 cps is used.

It is obvious that modifications could be made to what is described above in a general way without departing from the scope of the invention defined in the appended claims.

What is claimed is:

1. A pharmaceutical controlled release tablet for the oral administration of at least one active ingredient, said tablet comprising up to 60% by weight of said active ingredient mixed and compressed with at least 40% by weight of a carrier containing amylose cross-linked with from 0.1 to 10 grams of a cross-linking agent per 100 grams of amylose, wherein said carrier comprises:

30% to 90% of said cross-linked amylose; and from 10 to 30% of hydroxypropylmethylcellulose (HPMC) with a viscosity equal to or higher than 4000 cps, said percentage being expressed by weight with respect to the total weight of the tablet.

2. The tablet of claim 1, wherein the carrier also contains at least one additional ingredient selected from the group consisting of pharmaceutically acceptable fillers, glidants, binders, lubricants, anti-adherents and disintegrants.

3. The tablet of claim 2, wherein:

the active ingredient and the carrier containing the cross-linked amylose are in the form of powders which are mixed and compressed to obtain the tablet; and the cross-linked amylose contained in said carrier has been prepared with 1 to 6 grams of said cross-linking agent per 100 grams of amylose.

4. The tablet of claim 2, wherein said tablet is of the matrix type and the HPMC contained in the carrier has a viscosity higher than 4000 cps.

5. The tablet of claim 4, wherein the HPMC contained in the carrier is HMPC 2208.

6. The tablet of claim 5, wherein the HPMC contained in the carrier is HMPC 2208 and has a viscosity equal to 100000 cps.

7. The tablet of claim 6, comprising 20% by weight of HPMC 2208 with a viscosity equal to 100000 cps.

8. The tablet of claim 7, which contains 10% by weight of said active ingredient and wherein the cross-linked amylose contained in said carrier has been prepared with 3.5 grams of epichlorhydrin as said cross-linking agent per 100 grams of amylose.

9. The tablet of claim 4, wherein the HPMC contained in the carrier is HMPC 2910.

10. The tablet of claim 2, wherein said tablet is dry coated.

11. The tablet according to claim 10, which includes a core containing a given amount of said active ingredient and an external coating containing another amount of the same active ingredient or of another active ingredient mixed and compressed with said carrier containing said cross-linked amylose and HPMC.

12. The tablet of claim 11, wherein the core also comprises a carrier containing said cross-linked amylose.

13. The tablet of claim 12 wherein the HPMC contained in said carrier is selected from the group consisting of HPMC 2208 and HPMC 2910.

14. A method for preparing a pharmaceutical controlled release tablet for oral administration to a patient, said tablet comprising up to 60% by weight of at least one active ingredient and at least 40% by weight of a carrier containing amylose cross-linked with 0.1 to 10 grams of a cross-linking agent per 100 grams of amylose, said method comprising the step of adding hydroxypropylmethylcellulose (HPMC) with a viscosity equal to or higher than 4000 cps as an adjuvant to said carrier thereby controlling the effect of enzymes on said carrier.

15. The method of claim 14, wherein said tablet is of the matrix type and wherein the HPMC added to the carrier has a viscosity higher than 4000 cps.

16. The method of claim 15, wherein the HPMC added to the carrier is HPMC 2208.

17. The method of claim 16, wherein the HPMC 2208 added to the carrier has a viscosity equal to 100000 cps.

18. The method of claim 17, wherein 20% by weight of HPMC 2208 with a viscosity equal to 100000 cps is added to the carrier, said percentage being based on the total weight of the tablet.

19. The method of claim 15, wherein the HPMC added to the carrier is HPMC 2910.

20. The method of claim 14, wherein said tablet comprises a core containing an amount of said active ingredient and an external coating containing an amount of the same active ingredient or of a second active ingredient mixed and compressed with said carrier containing said cross-linked amylose to which HPMC has been added.

21. The method of claim 20, wherein the HPMC added to the carrier is selected from the group consisting of HPMC 2208 and HPMC 2910.

22. A pharmaceutical controlled release tablet for oral administration said tablet comprising:

from 30 to 90% of cross-linked amylose, wherein said amylose is cross-linked with from 0.1 to 10 grams of a cross-linking agent per 100 grams of amylose, and from 10 to 30% of hydroxypropylmethylcellulose (HPMC) with a viscosity equal to or higher than 4000 cps, said percentages being expressed by weight with respect to the total weight of the tablet.

* * * * *